(12) United States Patent
Zhu et al.

(10) Patent No.: US 11,083,500 B2
(45) Date of Patent: Aug. 10, 2021

(54) BIONIC ARTIFICIAL SPINAL JOINT

(71) Applicant: Hongwen Zhu, Tianjin (CN)

(72) Inventors: Hongwen Zhu, Tianjin (CN); Guofu Huang, Tianjin (CN); Ronghua Dong, Tianjin (CN); Tianmou Zhu, Tianjin (CN)

(73) Assignee: Hongwen Zhu, Tianjin (CN)

( * ) Notice: Subject to any disclaimer, the term of this patent is extended or adjusted under 35 U.S.C. 154(b) by 0 days.

(21) Appl. No.: 17/088,418

(22) Filed: Nov. 3, 2020

(65) Prior Publication Data

US 2021/0045780 A1 Feb. 18, 2021

(51) Int. Cl.
*A61B 17/70* (2006.01)

(52) U.S. Cl.
CPC ...... *A61B 17/7049* (2013.01); *A61B 17/7011* (2013.01); *A61B 17/7032* (2013.01)

(58) Field of Classification Search
CPC .............. A61B 17/7049; A61B 17/705; A61B 17/7052
USPC ........ 606/251, 256, 261, 265, 266, 270, 278
See application file for complete search history.

(56) References Cited

U.S. PATENT DOCUMENTS

| 6,802,844 | B2* | 10/2004 | Ferree | A61B 17/7005 |
| | | | | 606/258 |
| 7,083,621 | B2* | 8/2006 | Shaolian | A61B 17/1671 |
| | | | | 606/256 |
| 7,776,075 | B2* | 8/2010 | Bruneau | A61B 17/7014 |
| | | | | 606/279 |
| 8,012,177 | B2* | 9/2011 | Jackson | A61B 17/7031 |
| | | | | 606/254 |
| 9,526,533 | B1* | 12/2016 | Aranibar | A61B 17/7011 |
| 2006/0229609 | A1* | 10/2006 | Wang | A61B 17/7023 |
| | | | | 606/257 |
| 2008/0195208 | A1* | 8/2008 | Castellvi | A61B 17/7023 |
| | | | | 623/17.15 |
| 2010/0262187 | A1* | 10/2010 | Marik | A61B 17/7031 |
| | | | | 606/246 |

* cited by examiner

*Primary Examiner* — Eduardo C Robert
*Assistant Examiner* — David C Comstock
(74) *Attorney, Agent, or Firm* — CBM Patent Consulting, LLC (57) ABSTRACT

The invention discloses a bionic artificial spinal joint, wherein the spinal joint includes a plurality of fixing units, the fixing units are fixed on a vertebral body, at least two fixing units located on one side of a spine are arranged along the extension direction of the spine and fixed in sequence, and sufficient force can be borne between two adjacent fixing units. The overall micro-motion joint structure formed by two adjacent fixing units is both supportable and bendable. The present application imitates the function of the human inter-process joints, so that the spine equipped with the bionic artificial spine joint can be bent within a certain angle range while maintaining the height of the intervertebral space, thereby avoiding the problem of spinal rigidity after the traditional spine surgery pedicle internal fixation.

6 Claims, 7 Drawing Sheets

BIONIC ARTIFICIAL SPINAL JOINT

TECHNICAL FIELD

The present invention relates to a medical artificial joint prosthesis, in particular a bionic artificial spinal joint.

BACKGROUND ART

There are 24 vertebrae in the human spine, of which include 7 cervical vertebrae and 12 thoracic vertebrae. Sandwiched between two adjacent vertebrae are intervertebral discs, which are connected and fixed as a whole under the action of ligaments, joints and muscle tissues; the spine supports the skull in the upper end, connects the hip bones in the lower end, attaches the ribs in the middle, and serves as the back wall of the thorax, abdomen and pelvis; the spine has the functions of supporting the trunk, protecting the internal organs, protecting the spinal cord and performing exercise.

The front end of the vertebrae is called the vertebral body. The intervertebral disc is located between the vertebral bodies on two adjacent vertebrae. The vertebral body is connected at the back with a vertebral plate, through which a vertebral arch spinous process and a transverse process are connected. The vertebral arch surrounds to form a cone hole, and the cone holes on each vertebra are connected up and down to form a vertical spinal canal/spinal canal from top to bottom inside the spine, and the spinal cord is located in the spinal canal/vertebral canal.

The spinous process is directly behind the vertebrae, and multiple vertebra spinous processes are continuous in the vertical direction to form a longitudinal ridge, which is located in the middle of the back of the human body. The spinous processes of the cervical spine are short and bifurcated, near the horizontal position, the thoracic spinous processes are slender, obliquely behind and inferior, arranged in an imbricate shape; the lumbar spinous processes are plate-like horizontally backward; the transverse processes are located on both sides of the spinous processes. Both the spinous process and the transverse process are attachments of muscles and ligaments.

The spine is undoubtedly an extremely important part of the human body. In real life, there are many cases where the spine is affected by various degenerative diseases, trauma, etc., and there are various treatment and recovery methods after the spine is damaged. Among them, for more serious symptoms, surgical treatment of spinal lesions has become more and more common. With the gradual advancement of medical technology, people have higher expectations for postoperative recovery effects.

In spinal surgery, intervertebral discectomy, spinal canal enlargement, etc. are common types of a surgery, and for some surgeries, it is even required to remove the articular processes and lamina of several consecutive vertebral bodies; in the prior art, for such surgeries, it is required to use pedicle screws and fixation rods in the operation to increase the stability of the spine. Through the screw-rod technology, up-down/vertical support can be provided, i.e., to ensure that the spine after operation can resist sufficient pressure and tension in the vertical direction. Nevertheless, there are also notable shortcomings. The vertebrae might generally lose their normal bending function. Because the vertebrae with spinal prostheses cannot bend, the adjacent vertebrae on the upper and lower sides of the vertebra have to assume a greater compensatory bending angle, which will result in accelerated damage of the adjacent vertebrae, and will also bring discomfort to the patient, thereby leading to poor patient experience.

In addition, the existing spinal prostheses are more suitable for operations of single-piece vertebrae damage, and adapt poorly for operations where multiple vertebrae are required to be resected; and because the spinal prostheses are distributed on both sides, their ability for physical protection of the spine right at the back is weak. In particular, for patients undergoing laminectomy, in the absence of vertebral spinous processes and lamina, their back lacks a protective barrier to the spinal cord. The risk of spinal cord damage due to external forces is very high.

Due to the above-mentioned reasons, the inventors have conducted in-depth research on the existing spinal prostheses, hoping to design a bionic artificial spinal joint that can solve the above-mentioned problems.

SUMMARY OF THE INVENTION

In order to overcome the above-mentioned problems, the inventors of the present invention have conducted intensive research and designed a bionic artificial spinal joint. The spinal joint includes a plurality of fixing units which are fixed on a vertebral body by pedicle screws. At least two fixing units located on the same side of a spine are arranged along the extension direction of the spine and fixed in sequence. The fixing unit includes a support rod. The support rods on two adjacent fixing units abut against each other, so that sufficient force can be borne between two fixing units adjacent and fixed to each other to open the intervertebral space and the intervertebral foramen. One end of the support rod is provided with a spherical end, and the other end is provided with a hemispherical groove for accommodating the spherical end. As a result, the overall micro-motion joint structure formed by two adjacent fixing units is both supportive and bendable. The present application imitates the function of the human inter-process joint, so that the spine equipped with the bionic artificial spinal joint can bend within a certain angle range while maintaining the height of the intervertebral space. In addition, according to the patient's physical condition and the position of the vertebral body of the operation, the corresponding bendable angle can be set by the tightness of the spherical end and the bolt/filler; an outwardly convex fish-scale or shingle-shaped hard protective net is also arranged between the fixing units on both sides of the spine symmetrically to protect the spinal cord inside the middle from the impact from the back, thus completing the present invention.

Specifically, the object of the present invention is to provide a bionic artificial spine joint, which includes a plurality of fixing units 1, wherein the fixing units 1 are all fixed on a vertebral body, at least two fixing units 1 located on the same side of a spine are arranged along the extension direction of the spine and fixed in sequence;

sufficient force can be borne between two fixing units 1 adjacent and fixed to each other, and a supporting structure formed by the two fixing units 1 can be bent appropriately.

The fixing units 1 are symmetrically installed on both sides of the spine.

The fixing units 1 includes support rods 2, the support rods 2 are arranged along the extension direction of the spine, and the support rods 2 on two adjacent fixing units 1 abut against each other, so that sufficient force can be borne between the two adjacent fixing units 1.

A fixing joint 3 is sleeved on the support rod 2;

the support rod 2 is fixed to the vertebral body by setting the fixing joint 3;

preferably, the support rod 2 passes through the fixing joint 3;

the support rod 2 can slide back and forth in the fixing joint 3 along an axis of the support rod;

the fixing joint 3 can also be fixed to the support rod 2;

preferably, the fixing joint 3 is provided with a pedicle screw 4 that can be screwed into the vertebral body.

a spherical end 5 is provided at one end of the support rod 2;

a hemispherical groove 6 for accommodating the spherical end 5 is provided at the other end of the support rod 2;

by arranging the spherical end 5 and the hemispherical groove 6, a supporting structure formed by two adjacent fixing units 1 can be bent appropriately while bearing sufficient force.

On the support rod 2, a first connector 7 is provided behind the hemispherical groove 6;

a connecting cylinder 8 is sleeved on the support rod 2, and the connecting cylinder 8 can be wrapped around the outside of the spherical end 5, and a second connector that matches with the first connector 7 is provided on the connecting cylinder 8;

the second connector of the connecting cylinder 8 is fixed to the first connector 7 on the adjacent support rod, so that two adjacent fixing units 1 are fixed to each other, and the two support rods 2 abut against each other.

Bending angle of the supporting structure formed by the two fixing units 1 fixed to each other can be adjusted.

The spherical end 5 is in a shape of an ellipsoid, and the bending angle is adjusted by setting the shape and size of the spherical end 5.

the connecting cylinder 8 is provided with a large open end 81 and a small open end 82, the second connector is arranged on the large open end 82, the small open end 81 is sleeved on the outside of the support rod 2, and the bending angle is adjusted by setting a gap between the support rod 2 and the small open end 81.

An outwardly convex fish scale or shingled hard protective net 9 is arranged between the fixing units 1 symmetrically installed on both sides of the spine.

The beneficial effects of the present invention include:

(1) the supporting structure formed by each fixing unit in the bionic artificial spine joint provided by the present invention can be bent moderately under the condition of bearing sufficient force to imitate the micro-motion bending effect of the human spine joint, so as to further strengthen the bionic effect of the bionic joint, thus avoiding the problem of spinal rigidity caused by traditional spinal surgery pedicle internal fixation;

(2) in the bionic artificial spine joint provided by the present invention, the height of the vertebral body space and the intervertebral foramen can be increased by fixation with a fixing unit;

(3) the bionic artificial spine joint provided by the present invention can be provided with a corresponding bendable angle value according to the patient's physical condition and the position of the vertebral body of the operation, so that it has basically the same functional effect as the spine joint of natural human growth; and (4) according to the bionic artificial spine joint provided by the present invention, an outwardly convex hard protective net is also arranged between the fixing units symmetrically installed on both sides of the spine to protect the spinal cord inside the middle part and prevent external force from stimulating the spinal cord.

DESCRIPTION OF THE REFERENCE SIGNS

1—fixing unit
2—support rod
3—fixing joint
31—first opening
32—second opening
33—slot
34—filler
35—limiting slot
4—pedicle screw
5—spherical end
6—hemispherical groove
7—first connector
8—connecting cylinder
81—large open end
82—small open end
9—hard protective net

DETAILED DESCRIPTION

The present invention will be further described in detail below through the drawings and embodiments. Through these descriptions, the characteristics and advantages of the present invention will become clearer.

The term "exemplary" herein means "serving as an example, embodiment, or illustration." Any embodiment described herein as "exemplary" need not be construed as being superior to or better than other embodiments. Although various aspects of the embodiments are shown in the drawings, unless otherwise noted, the drawings are not necessarily drawn to scale.

Figure 1:
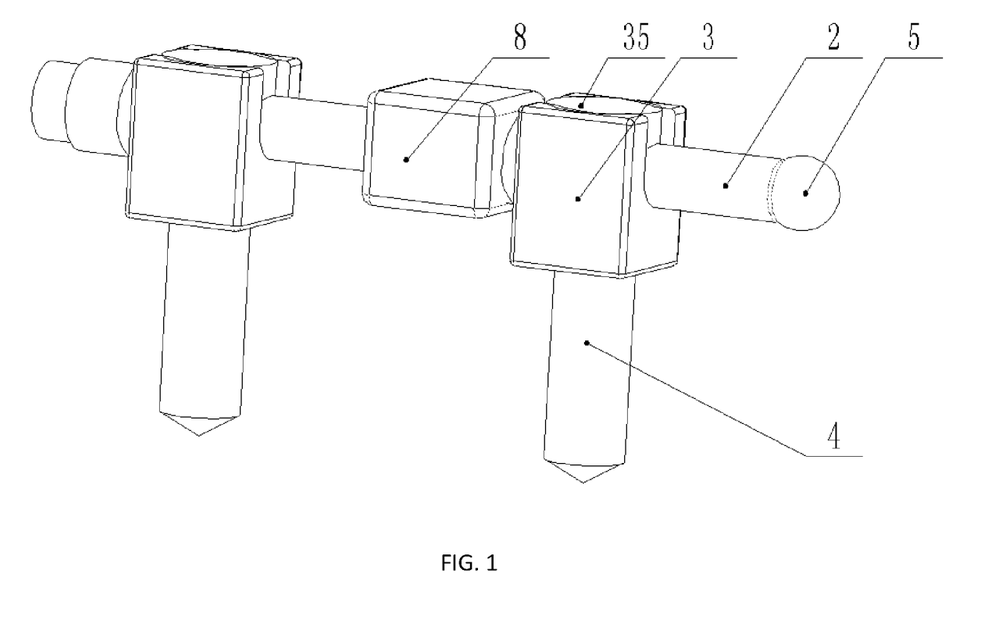
FIG. 1 shows a schematic structural diagram of two fixing units in a bionic artificial spine joint according to a preferred embodiment of the present invention.
Figure 2:
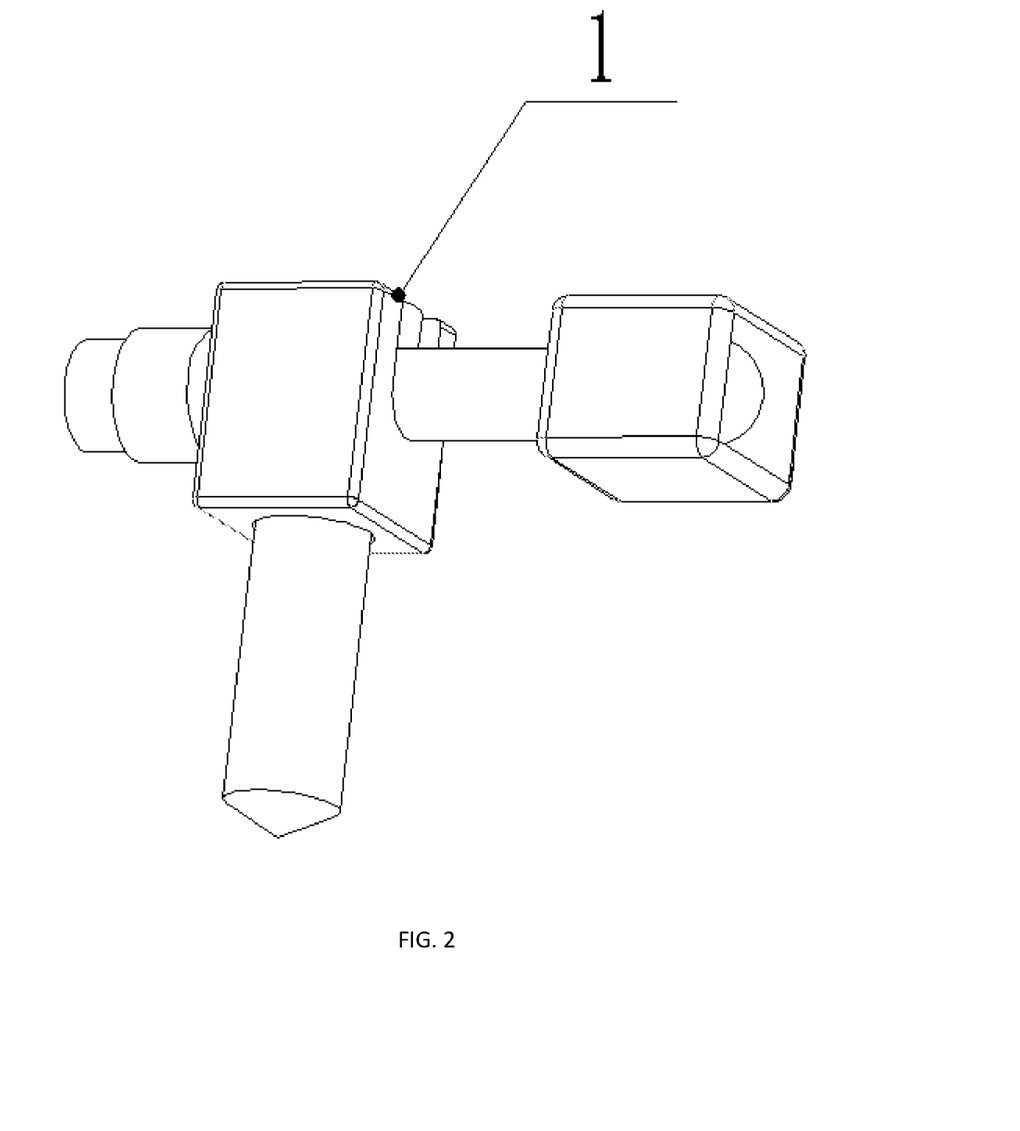
FIG. 2 shows a schematic structural diagram of a complete fixing unit in a bionic artificial spine joint according to a preferred embodiment of the present invention.

According to the bionic artificial spine joint provided by the present invention, the spine joint includes a plurality of fixing units 1. According to the number and length of the fixing stage, a corresponding number of fixing units can be selected. FIG. 2 shows a complete fixing unit. FIG. 1 shows a schematic structural diagram when two fixing units 1 are fixed to each other, wherein a connecting cylinder is omitted in one of the fixing units.

The fixing unit 1 is fixed on the vertebral body.

At least two fixing units 1 located on the same side of the spine are arranged along the extension direction of the spine and fixed in sequence.

The two fixing units 1 fixed to each other can bear a sufficiently force, which includes tension and pressure. When the force is pressure, the fixing units abut against each other, and the pressure is transmitted downward or upward to ensure that the distance between the two fixing units will not be compressed under the pressure, and the vertebral structure between them will not be compressed and destroyed. In addition, the intervertebral space and the intervertebral foramen need to be separated by the fixing unit 1.

When the force is a tension, the fixing units are fixed to each other and kept in contact with each other. The tension is transmitted downward or upward to ensure that the distance between two fixing units will not be stretched under the tension. The structure of the vertebral body will not be damaged by stretching.

The supporting structure formed by the two fixing units 1 can be bent moderately, and the bending amplitude is small, generally less than 10 degrees; it is used to imitate the small bending function of the human spine, and it can still ensure the extension of the bearing spine during the bending process. The tension and pressure in the direction prevent spinal injury.

Preferably, since the composition of each fixing unit is the same, any number (greater than 2) of the fixing units can be provided in the direction in which the spine extends.

Preferably, the plurality of fixing units 1 are installed symmetrically on both sides of the spine; in order to ensure uniform force on both sides, the number of fixing units on both sides of the spine needs to be exactly the same.

Figure 5:
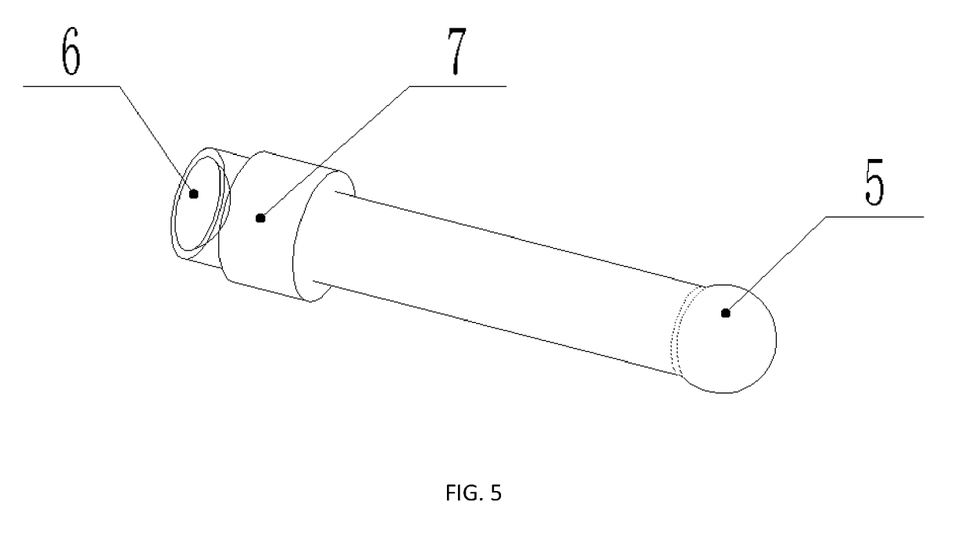
FIG. 5 shows a schematic diagram of a supporting rod structure in a bionic artificial spine joint according to a preferred embodiment of the present invention.

In a preferred embodiment, as shown in FIGS. 1, 2 and 5, the fixing unit 1 includes a support rod 2, and the main body of the support rod 2 is preferably a smooth straight rod with a cylindrical cross-section.

Preferably, the support rod is made of high-strength materials such as metal, and the support rod can bear sufficient force.

The support rods 2 are arranged along the extension direction of the spine, and the support rods 2 on the two adjacent fixing units 1 abut against each other. After the installation is completed, the support rods 2 abutting against each other cannot be separated again; the abutment is used to transfer force between two adjacent fixing units, so that two adjacent fixing units 1 can bear sufficient force. The area connecting the two support rods 2 can also be called a micro joint, and the two support rods 2 can also have a certain degree of mobility, that is, they can rotate relatively in a small range.

Figure 3:
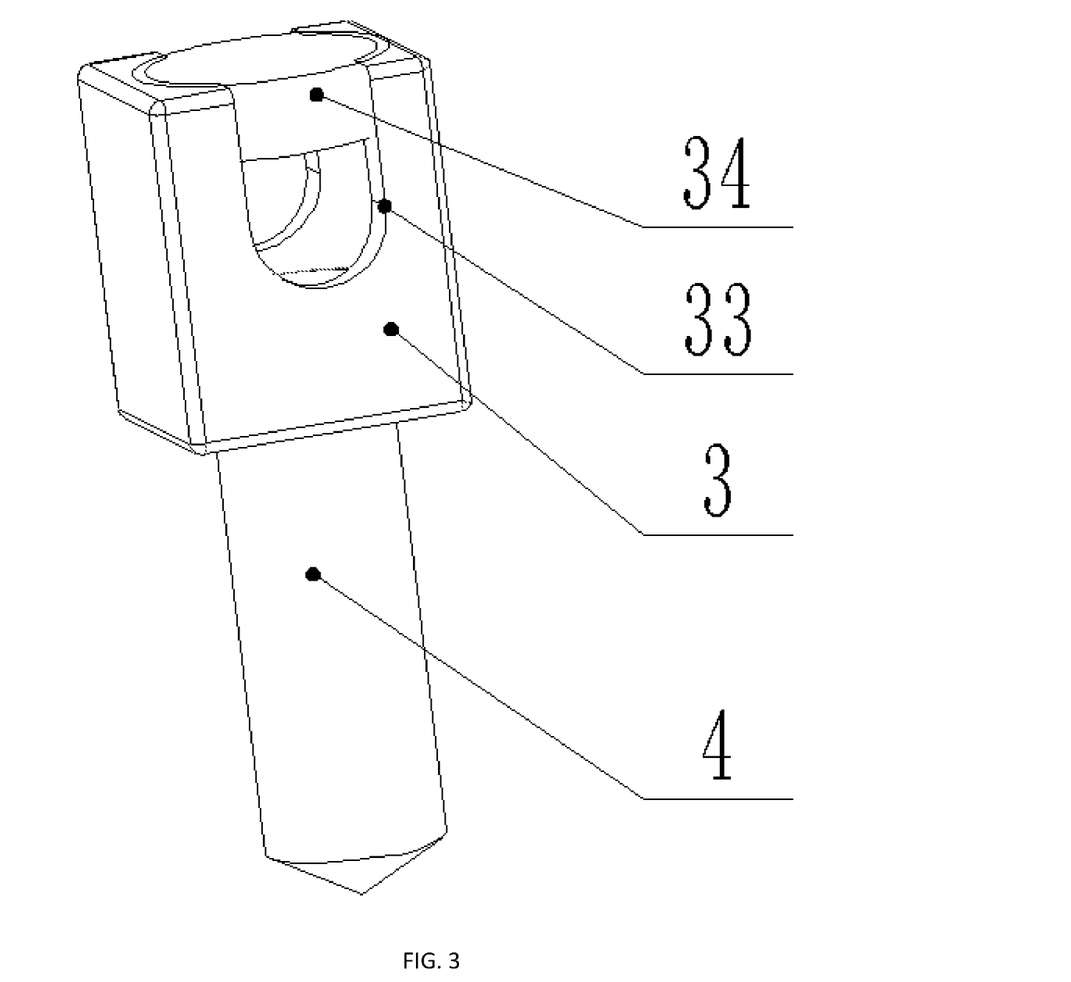
FIG. 3 shows a schematic structural diagram of a fixing joint and a pedicle screw on the bionic artificial spine joint according to a preferred embodiment of the present invention.
Figure 4:
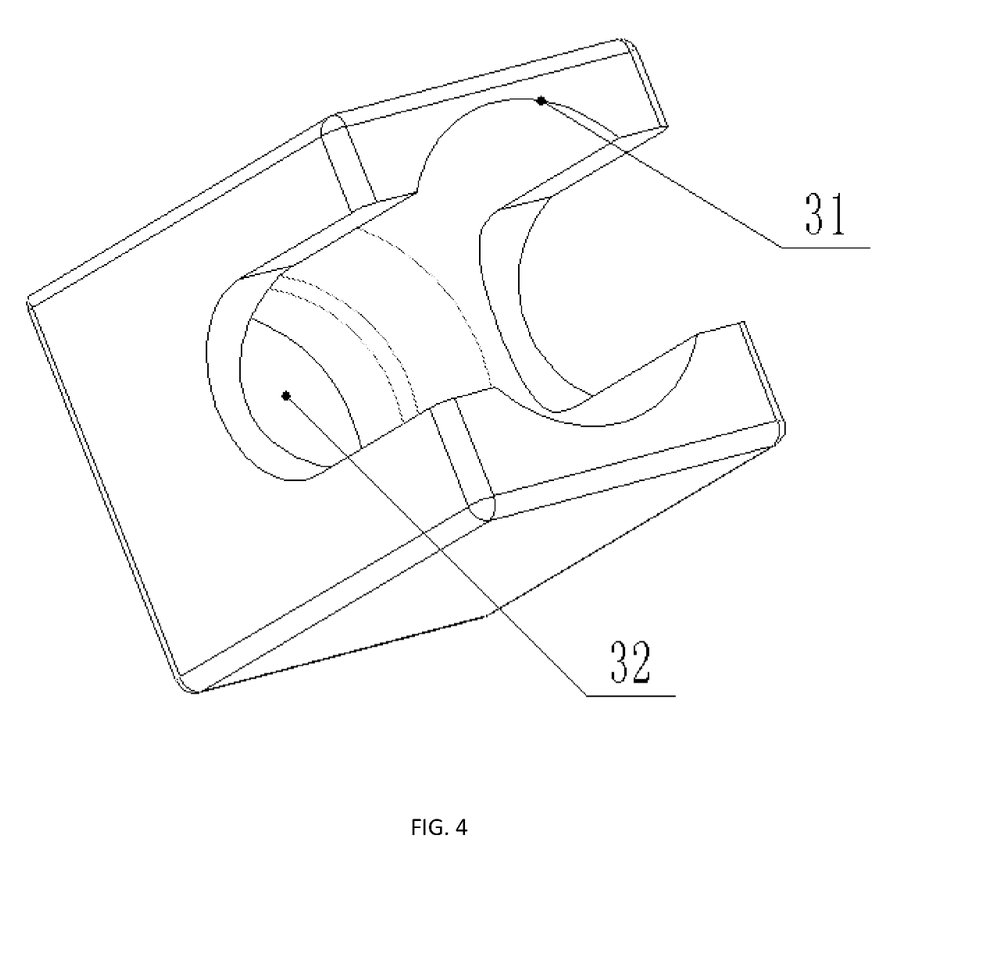
FIG. 4 shows a schematic diagram of a fixing joint structure in a bionic artificial spine joint according to a preferred embodiment of the present invention.

In a preferred embodiment, as shown in FIGS. 1, 3 and 4, a fixing joint 3 is sleeved on the support rod 2.

The support rod 2 is fixed to the vertebral body by setting the fixing joint 3.

Preferably, the support rod 2 passes through the fixing joint 3.

The support rod 2 can slide back and forth in the fixing joint 3 along an axis of the support rod.

The fixing joint 3 can also be fixed to the support rod 2.

Preferably, a pedicle screw 4 that can be screwed into the vertebral body is provided on the fixing joint 3.

Preferably, as shown in FIG. 4, the fixing joint 3 is in the shape of a hollow cylinder with open ends, and its cross-sectional shape can be round, oval, rectangular, etc., and the fixing joint 3 has a larger opening at one end, which is called the first opening 31, and the other end is smaller, which is called the second opening 32. The pedicle screw 4 includes an elongated body portion with threads and a nut at the end, wherein the main part of the pedicle screw 4 can pass through the second opening 31 of the fixing joint 3, but the nut of the pedicle screw 4 cannot pass through the second opening 31, so that the pedicle screw 4 and the fixing joint 3 are fixed. When the pedicle screw 4 is screwed and fixed on the vertebral body, and the pedicle screw 4 is completely screwed into the vertebral body, the pedicle screw 4 can achieve the object of fixing the fixing joint 3 on the vertebral body.

On the fixing joint 3, as shown in FIGS. 1, 3, and 4, two slots 33 are set on the wall surface along the axial direction of the fixing joint 3 from the first opening 31. The two slots 33 are symmetrically arranged, and the widths of the slots are the same; their widths are just enough to allow the support rod 2 to pass through, preferably, the widths are just enough to allow the main body of the support rod 2 to pass through, namely, the support rod 2 passes through the fixing joint 3 by fitting with the slot 33, so that the support rod 2 can slide back and forth along the axis of the support rod in the fixing joint 3, and can be adjusted to the best position;

Preferably, a filler 34 is provided at the first opening 31 of the fixing joint 3, and the filler 34 is fixed to the fixing joint 3 to block the first opening 31 and pressed to pass through the support rod 2 of the fixing joint 3 so that the fixing joint 3 and the support rod 2 are fixed to each other.

More preferably, the filler 34 may have a buckle structure or a thread structure. When the filler 34 is provided with an external thread, the inner wall of the fixing joint 3 is further provided with a corresponding internal thread; wherein the filler 34 can be a hexagon socket screw.

The process of using the fixing joint comprises first subjecting the pedicle screw 4 to pass through the first opening 31 and the second opening 32 of the fixing joint 3, and then fixing the pedicle screw 4 to the vertebral body. The pedicle screw is screwed down by an equipment such as a screwdriver so that both the pedicle screw and the fixing joint 3 are fixed on the vertebral body. Then the support rod 2 is embedded in the slot 33, so that the support rod 2 passes through the fixing joint 3. After adjusting the position of the support rod in the vertical direction, the filler 34 is fixed on the fixing joint 3, thereby compressing and fixing the support rod 2, so that the support rod 2 is fixed to the fixing joint 3 and the vertebral body as a whole.

In a preferred embodiment, as shown in FIGS. 1, 2 and 5, a spherical end 5 is provided at one end of the support rod 2, and the cross-sectional size of the spherical end 5 is greater than that of the support rod.

A hemispherical groove 6 for accommodating the spherical end 5 is provided at the other end of the support rod 2;

By arranging the spherical end 5 and the hemispherical groove 6, a supporting structure formed by two adjacent fixing units 1 can be bent appropriately while bearing sufficient force.

The abutment between the support rods between two adjacent fixing units 1 is specifically realized by the spherical end 5 and the hemispherical groove 6 being matched with each other, and a part of the spherical end 5 is embedded in the hemispherical groove 6, the longitudinal load can be transmitted therebetween and relative bending can be achieved.

In a preferred embodiment, as shown in FIGS. 1, 5, 6 and 7, on the support rod 2, a first connector 7 is provided behind the hemispherical groove 6.

a connecting cylinder 8 is sleeved on the support rod 2, and the connecting cylinder 8 can be wrapped around the outside of the spherical end 5, and a second connector that matches with the first connector 7 is provided on the connecting cylinder 8.

The second connector of the connecting cylinder 8 is fixed to the first connector 7 on the adjacent support rod, so that two adjacent fixing units 1 are fixed to each other, and the two support rods 2 abut against each other.

Figure 6:
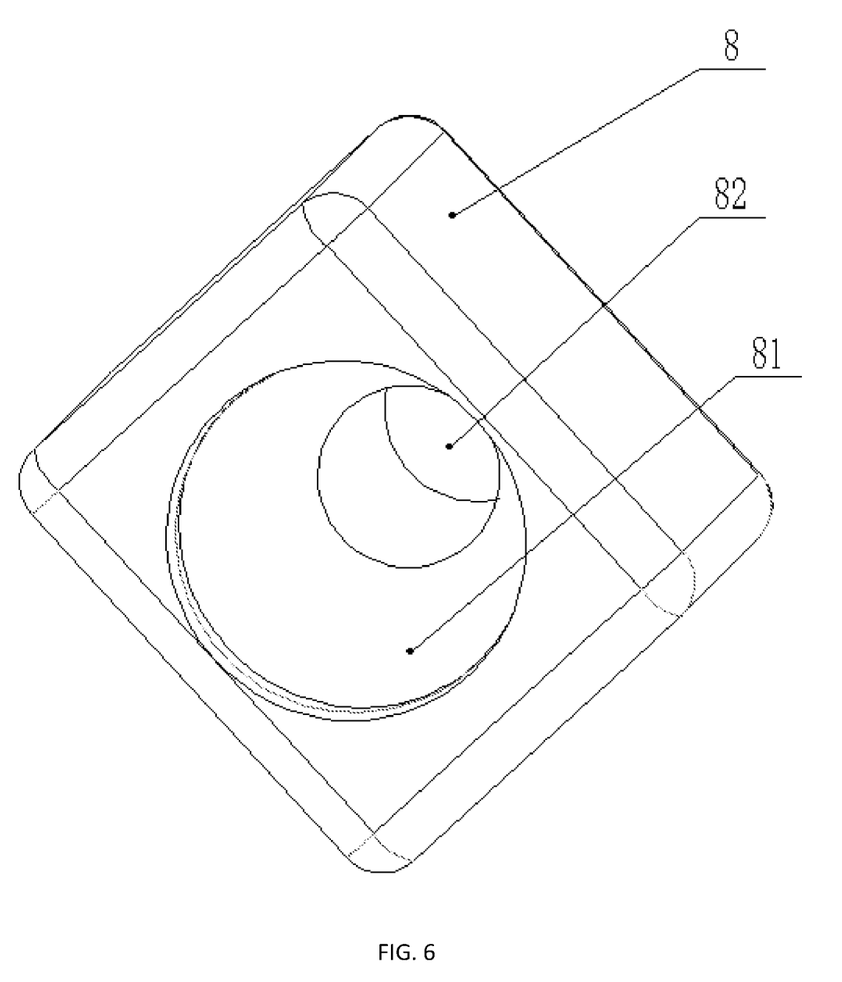
FIG. 6 shows a schematic structural diagram of a connecting cylinder in a bionic artificial spine joint according to a preferred embodiment of the present invention.

The connecting cylinder 8 is in the shape of a hollow cylinder with open ends, and its cross-sectional shape can be round, oval, rectangular, etc., and the connecting cylinder 8 is provided with a large accommodating space for accommodating the spherical end 5 and the hemispherical groove 6, as well as a small accommodating space for accommodating the connecting rods.

Both ends of the connecting cylinder 8 are open, wherein the open end directly connected to the large accommodating space is the large open end 81, and the other open end connected to the small accommodating space is the small open end 82, wherein the inner diameter of the small open end 82 is lessthan the outer diameter of the spherical end 5, so that the connecting cylinder 8 is sleeved on the support rod 2 and cannot be separated from the support rod 2.

The spherical end 5 is located inside the connecting cylinder 8, and the connecting cylinder 8 is fixed on the first connector 7 of another fixing unit, so that the spherical end 5 and the hemispherical groove 6 on the other fixing unit abut against each other and are all accommodated in the connecting cylinder 8, so as to ensure that the spherical end 5 and the hemispherical groove 6 remain abutting against each other, are not separated, and will not be separates from each other when they are relatively bent.

Preferably, the first connector 7 and the second connector may be buckle-type devices that cooperate with each other and are connected by contact buckles; or they may be flanges and other devices that are fixed by bolts; or they may be a threaded device with threaded fit. For example, the first connector 7 may be an external thread provided on the support rod 2, and the second connector may be an internal thread provided on the inner wall of the connecting cylinder 8. By screwing and fixing the connecting cylinder 8 on the external thread on the support rod 2, the abutment and fixation between the spherical end 5 and the hemispherical groove 6 are completed, so that the two adjacent fixing units can bear the force and be bendably fixed.

In order to enable the supporting structure formed by the two fixing units to be smoothly bent, the inner diameter of the small open end 81 is slightly greater than the outer diameter of the support rod 2.

In a preferred embodiment, the supporting structure formed by the two fixing units 1 fixed to each other allows the bending angle to be adjustable. There can be multiple adjustment methods and adjustment principles.

Preferably, the spherical end 5 is in a shape of an ellipsoid, and the bending angle is adjusted by setting the shape and size of the spherical end; the head area of the spherical end 5 of the ellipsoid extends into the hemispherical groove 6, the relative rotation angle between the spherical end 5 of the ellipsoid and the hemispherical groove 6 is limited, and can be adjusted by changing the ellipsoidal size/shape of the spherical end 5 of the ellipsoid, thereby adjusting the bending angle of the supporting structure formed by two fixing units 1.

Preferably, the connecting cylinder 8 is provided with a large open end 81 and a small open end 82.

The second connector is arranged on the large open end 82.

The small open end 81 is sleeved on the outside of the support rod 2, and the bending angle is adjusted by setting a gap between the support rod 2 and the small open end 81. The gap can determine the upper limit of the bending angle. The greater the gap, the greater the theoretically movable angle, and the smaller the gap, the smaller the theoretically movable angle. The corresponding bendable angle can be set according to the patient's physical condition and the position of the vertebra body for operation so that it has basically the same functional effect as the spine joint for natural human growth, thereby achieving a high degree of bionics.

In a preferred embodiment, the number of the fixing units 1 can be determined according to the number of surgical vertebral bodies and the patient's application status. A plurality of fixing units 1 can be provided at the same time on one side of the spine, e.g., continuous 3 to 5 fixing units. And each fixing unit can bear sufficient force, and the supporting structure formed by two adjacent fixing units 1 can be bent appropriately, so that the spine can still be bent appropriately after the operation.

Figure 7:
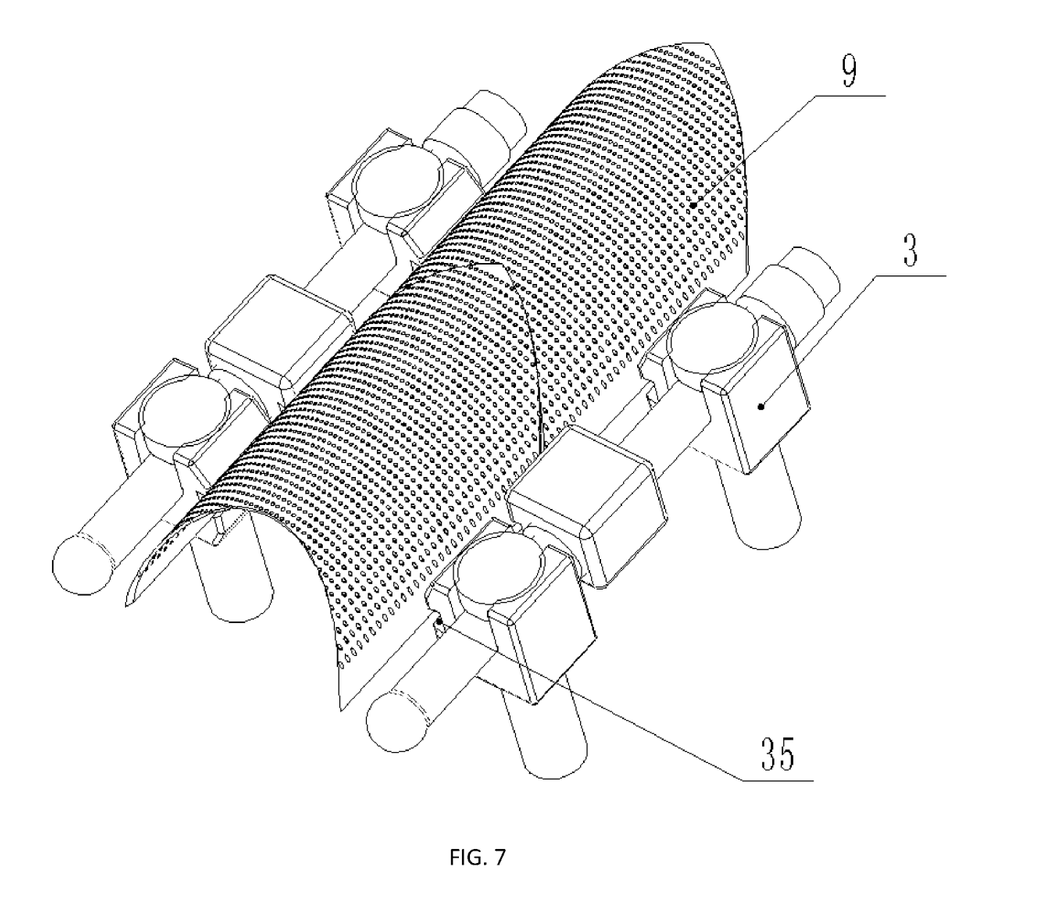
FIG. 7 shows a schematic diagram of the overall structure of a bionic artificial spine joint according to a preferred embodiment of the present invention.

In many spine surgeries, part of the articular processes and lamina are removed in order to complete the spinal canal enlargement, which destroys the three-dimensional structure of the spine and the protective mechanism of the spinal cord. Only the back muscle tissue can provide protection to the spinal cord. The protective ability of the human body for the right back weakens, and the spinal cord is particularly fragile but is a structural organ that must be specially protected. However, the right back of the human body is also more susceptible to external stimulation. Therefore, it is particularly important to enhance the protection of the spinal cord in the back after surgery. In a preferred embodiment, as shown in FIG. 7, an outwardly convex hard protective net 9 is provided between the fixing units 1 symmetrically installed on both sides of the spine to protect the spinal cord inside the middle part and prevent external forces from stimulating the spinal cord.

A hard protective net 9 is provided between the two fixing units 1 symmetrical about the spine. Since there are multiple pairs of fixing units 1, the hard protective net 9 has multiple pieces. The hard protective net 9 is in the shape of fish scales or shingles. The hard protective nets 9 are stacked one after another. The front of the rear hard protective net 9 is pressed against the rear of the front hard protective net 9 to jointly cover the missing outer part of the spinal structure lacking a spinous process, thereby providing physical protection for the spinal cord.

Preferably, a limiting slot 35 is provided on the fixing joint 3 on the fixing unit 1, and the limiting slot 35 is located on the side facing the spine. A hard protective net 9 is arranged between two fixing joints 3 on two fixing units symmetrically provided on the spine, where the edges on both sides of the hard protective net 9 are embedded in the limiting slot, or the protective net can be fixed by the combination of slot and micro screw fixation. The hard protective net 9 has a relatively large elastic arc structure, which bulges outward under the pressure of the limiting slots on both sides, so that its cross-sectional shape is an outwardly convex arc.

In the description of the present utility model, it should be noted that the terms "upper," "lower," "inner," "outer," "front," "rear" and other directions or positional relationships are based on the present utility model, only for the convenience of describing the utility model and simplifying the description, rather than indicating or implying that the device or element pointed out must have a specific orientation, be constructed and operated in a specific orientation, and therefore cannot be understood as limiting the utility model. In addition, the terms "first" and "second" are only used for descriptive purposes, and cannot be understood as indicating or implying relative importance.

The above describes the present invention in combination with preferred embodiments, but these embodiments are only exemplary and merely serve for illustration. On this basis, various replacements and improvements can be made to the present invention, all of which fall within the protection scope of the present invention.

What is claimed is:

1. A bionic artificial spinal joint, characterized in that the spinal joint includes a plurality of fixing units (1);
   the fixing units (1) are all configured to be fixed on a vertebral body;
   at least two fixing units (1) are configured to be located on the same side of a spine are arranged along the extension direction of the spine and fixed in sequence;
   sufficient force can be borne between two fixing units (1) adjacent and fixed to each other, and a supporting structure formed by the two fixing units (1) can be bent appropriately;
   wherein:
   the fixing units (1) includes support rods (2),
   the support rods (2) are configured to be arranged along the extension direction of the spine, and the support rods (2) on two adjacent fixing units (1) abut against each other, so that sufficient force can be borne between the two adjacent fixing units (1);
   a spherical end (5) is provided at one end of a first support rod (2);
   a hemispherical groove (6) for accommodating the spherical end (5) is provided at the other end of the first support rod (2);
   by arranging the spherical end (5) and the hemispherical groove (6), the supporting structure formed by two adjacent fixing units (1) can be bent appropriately while bearing sufficient force;
   on the support rod (2), a first connector (7) is provided behind the hemispherical groove (6);
   a connecting cylinder (8) is sleeved on a second support rod (2), and the connecting cylinder (8) can be wrapped around the outside of the spherical end (5), and a second connector that matches with the first connector (7) is provided on the connecting cylinder (8);
   the second connector of the connecting cylinder (8) is fixed to the first connector (7) on the adjacent support rod, so that two adjacent fixing units (1) are fixed to each other, and the first and second support rods (2) abut against each other;
   the connecting cylinder (8) is provided with a large open end (81) and a small open end (82),
   the second connector is arranged on the large open end (82),
   the small open end (81) is sleeved on the outside of the second support rod (2), and the bending angle is adjusted by setting a gap between the second support rod (2) and the small open end (81).

2. The spinal joint according to claim 1, wherein:
   the fixing units (1) are configured to be symmetrically installed on both sides of the spine.

3. The spinal joint according to claim 2, wherein:
   an outwardly convex fish scale or shingled hard protective net (9) is configured to be arranged between the fixing units (1) symmetrically installed on both sides of the spine.

4. The spinal joint according to claim 1, wherein:
   a fixing joint (3) is sleeved on any of the support rods (2);
   any of the support rods (2) is configured to be fixed to the vertebral body by setting the fixing joint (3);
   preferably, any of the support rods (2) passes through the fixing joint (3);
   any of the support rods (2) can slide back and forth in the fixing joint (3) along an axis of any of the support rods (2);
   the fixing joint (3) can also be fixed to any of the support rods (2);
   preferably, the fixing joint (3) is provided with a pedicle screw (4) that can be configured to be screwed into the vertebral body.

5. The spinal joint according to claim 1, wherein:
   the bending angle of the supporting structure formed by the two fixing units (1) fixed to each other can be adjusted.

6. The spinal joint according to claim 5, wherein:
   the bending angle is adjustable by altering the size of the spherical end (5).

* * * * *